US008608677B2

(12) United States Patent
Motyer

(10) Patent No.: US 8,608,677 B2
(45) Date of Patent: Dec. 17, 2013

(54) DEVICE FOR CARRYING THE LOAD OF INJURED SOFT TISSUE

(76) Inventor: Neil Motyer, Melbourne (AU)

( * ) Notice: Subject to any disclaimer, the term of this patent is extended or adjusted under 35 U.S.C. 154(b) by 343 days.

(21) Appl. No.: 12/312,291

(22) PCT Filed: Nov. 13, 2007

(86) PCT No.: PCT/AU2007/001731
§ 371 (c)(1),
(2), (4) Date: May 4, 2009

(87) PCT Pub. No.: WO2008/058319
PCT Pub. Date: May 22, 2008

(65) Prior Publication Data
US 2010/0069802 A1  Mar. 18, 2010

(30) Foreign Application Priority Data
Nov. 17, 2006  (AU) ................................ 2006906403

(51) Int. Cl.
A61F 5/00 (2006.01)
(52) U.S. Cl.
USPC .................................. 602/20; 602/5; 128/878
(58) Field of Classification Search
USPC ................ 128/845, 869–870, 877–879, 882;
602/60, 20–21, 61–62, 4–5;
D24/190–191
See application file for complete search history.

(56) References Cited

U.S. PATENT DOCUMENTS

| 3,724,453 | A | * | 4/1973 | Dixon et al. | 602/19 |
|---|---|---|---|---|---|
| 4,720,106 | A | * | 1/1988 | Bickham | 473/521 |
| 4,807,607 | A | * | 2/1989 | Roder | 602/20 |
| 5,172,703 | A | * | 12/1992 | Tiede et al. | 128/875 |
| 5,248,292 | A | * | 9/1993 | Holland | 602/20 |
| 5,358,470 | A | * | 10/1994 | Johnson | 602/20 |
| 5,513,657 | A | * | 5/1996 | Nelson | 128/879 |
| 5,513,786 | A | * | 5/1996 | Drane | 224/188 |
| 5,624,388 | A | * | 4/1997 | Lehr | 602/20 |
| 5,755,679 | A | * | 5/1998 | Selner et al. | 602/27 |
| 5,776,087 | A | * | 7/1998 | Nelson et al. | 602/19 |
| 5,830,165 | A | * | 11/1998 | Rowe et al. | 602/4 |
| 5,891,079 | A | * | 4/1999 | Barnes | 602/61 |
| 6,024,715 | A | * | 2/2000 | Maxwell | 602/64 |
| 6,106,493 | A | * | 8/2000 | Rozell | 602/20 |
| 6,142,965 | A | * | 11/2000 | Mathewson | 602/62 |
| D445,191 | S | * | 7/2001 | Rodgers | D24/192 |
| 6,306,111 | B1 | * | 10/2001 | Dean | 602/20 |
| 6,783,507 | B1 | * | 8/2004 | Fisher | 602/22 |
| 2005/0197608 | A1 | * | 9/2005 | Taylor et al. | 602/21 |

FOREIGN PATENT DOCUMENTS

| CN | 1164385 | 11/1997 |
|---|---|---|
| JP | 2006006375 | 1/2006 |
| RU | 2158119 | 10/2000 |

* cited by examiner

Primary Examiner — Tatyana Zalukaeva
Assistant Examiner — Camtu Nguyen
(74) Attorney, Agent, or Firm — Kusner & Jaffe

(57) ABSTRACT

The present invention relates to the field of therapeutic and/or injury support devices. In one form, the invention relates to a device for the relative protection and treatment of injured muscles, tendons and other soft tissue, as well as a method of utilizing this device. In one particular form, the present invention relates to providing an external support structure to assist in the load carrying function of injured soft tissue.

9 Claims, 10 Drawing Sheets

DEVICE FOR CARRYING THE LOAD OF INJURED SOFT TISSUE

FIELD OF INVENTION

The present invention relates to the field of therapeutic and/or injury support devices.

In one form, the invention relates to a device for the relative protection and treatment of injured muscles, tendons and other soft tissue, as well as a method of utilizing this device. In one particular form, the present invention relates to providing an external support structure to assist in the load carrying function of injured soft tissue.

It will be convenient to hereinafter describe the invention in relation to a therapeutic and/or injury support device, however it should be appreciated that the present invention is not limited to that use only.

BACKGROUND ART

The discussion throughout this specification comes about due to the realisation of the inventors and/or the identification of certain prior art problems by the inventors.

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

Existing support straps and similar devices and systems designed to protect injuries such as tendonitis and epicondylitis are considered not particularly effective. The most common method in current use is a tensioned strap which is placed around healthy tissue, for example, in the forearm and which has the effect of restricting muscle contraction. This is considered uncomfortable and only gives minor restriction to tensioning of the injured tissue. A device of this nature titled 'Therapeutic Support Device' is disclosed in U.S. Pat. No. 3,789,842.

It is considered by some that the above mentioned tensioned strap device also has some load carrying benefit, whereby the healthy portion of muscle anchors or pulls from the strap (which acts as a floating anchor) instead of the true origin of the muscle, and some part of the tension force involved (normally carried by the injured portion of muscle or tendon) is transferred to and carried by the healthy tissue around the injured tissue on the other side of the strap. Unfortunately, in practice, it has been realised that the load carrying support provided with this type of device is generally not sufficient to be useful.

A number of devices have been designed to apply pressure directly onto injured tissue and hold joints together. For example, in U.S. Pat. No. 5,624,388, such a device titled 'Therapeutic elbow support method' has been disclosed using elastic material around a joint in a FIG. 8 pattern. In AU733693 a device titled 'Support brace for knee or elbow' has been proposed, and still in U.S. Pat. No. 3,945,046 another device titled 'Flexible knee support' has been disclosed, both devices using elastic sleeves and elastic support straps. A similar design titled 'Method for providing stability to the elbow joint' and disclosed in U.S. Pat. No. 5,891,079 uses a FIG. 8 elastic strap over an elastic sleeve to stabilize an elbow joint. These designs and many similar to them are useful in holding the joints together and therefore providing support to damaged ligaments, however these types of devices are not considered to have an effective anchor system which can be connected to the elastic material, and therefore do not provide a satisfactory load carrying support for the tendons and muscles.

A more effective approach of actually carrying the load of injured muscles and tendons with rigid adhesive taping using two anchors and a tie has gained some usage, particularly in the sporting fraternity. Unfortunately, however, this method of taping does not work properly in providing consistent support for different limb or body positions. In addition this method of taping tends to be messy, restrict limb or body movement, irritate the skin, and can be tedious and expensive, as it usually needs to be applied by a skilled therapist or sports trainer. Furthermore, although elastic adhesive taping currently on the market is considered to be more comfortable, it only provides very gentle support, and is also messy, tedious and expensive.

Alternate designs with two prefabricated anchor/mooring devices pulled together with several elastic ties across a joint have been disclosed in BE1010652 in an invention titled 'Device for unburdening muscles and tendons that work in conjunction with a joint'. A similar invention titled 'Shoulder stabilizer method', shown in U.S. Pat. No. 5,628,725, proposes a garment covering the arm and chest (with an inside surface constructed of a rubberized material for gripping the skin) and one or more tensioned elastic straps wrapped around the body and connecting the arm and chest. Another similar invention titled 'Shoulder stabilizer' is shown in U.S. Pat. No. 6,106,493. These inventions are considered to be intended to carry some of the load of injured tendons without the use of adhesive tape, but unfortunately the designs have an elaborate system of anchors, mooring devices and ties, and as such are considered to be very cumbersome and impractical, and have thus not gained wide acceptance and remain largely unknown.

An object of the present invention is to provide a relatively simple but effective method of unloading injured tendons and other soft tissue that is both comfortable and easy to use.

A further object of the present invention is to alleviate at least one disadvantage associated with the prior art.

SUMMARY OF INVENTION

The present invention provides, in a first inventive aspect, a method and/or device adapted to enable support of a portion of a human body, the device comprising a first anchor portion adapted to provide an anchor point proximate a first body portion, and a second extendable portion adapted to extend to a second body portion, the portion of the body being supported being substantially between the first and second body portions.

The present invention provides, in a second inventive aspect, a method and/or device adapted to carry the load and/or reduce the tension of injured soft tissue, the device comprising an anchor, and a carry strap having an elastic portion, the carry strap having both ends being adapted to be connectable to the said anchor at an angle substantially between 30 and 150 degrees.

In a preferred form of the invention, conventional tension straps of the type currently in common use to restrict muscle contraction, including variations which provide heat or additional pressure to injured tissue, may be used as anchor components in the manufacture of the present device provided that they produce the desired outcome.

The anchors will preferably be made from soft, flexible non elastic material, but a number of other materials such as elastic materials and adhesive or non adhesive tape may be used, provided that they produce the desired outcome.

The elastic carry strap or tie is preferably made from a soft, stretchable elastic or fabric, but other materials that perform a similar function may be used.

The elastic carry strap is shaped to fit comfortably on the part of the body over which it is stretched, as can be seen in examples of embodiments and applications as shown in FIGS. 2, 3 and 4.

The anchors and elastic carry strap or tie are fitted to ensure that they are comfortable and do not slip.

The elastic carry strap or tie is tensioned to provide the desired load carrying relief to the injured tissue. The tension can be adjusted substantially by varying the position of attachment of the end of the elastic carry strap (4) to the Velcro surface of the anchor strap (5).

Other aspects and preferred aspects are disclosed in the specification and/or defined in the appended claims, forming a part of the description of the invention.

In essence, the present invention provides an improvement compared to a conventional tensioned strap (to restrict muscle contraction) because it provides an adjustable external force to carry the load of the injured tissue and protect it from excessive strain. It has been realised that the prior art is designed to hold or restrict movement of body tissue/body portions, whereas the present invention is designed to unload body tissue/body portions. The present invention utilizes an elastic support system which, while allowing movement of the injured portion of the body, also provides assistance in carrying load associated with the injured body portion. In one form, the present invention provides a device and/or method in which the load of an injured portion of a body is carried by an elastic carry strap by attaching the elastic carry strap to an anchor (a device which locks onto a local section of the body with a friction grip) on one side of the injury, with the said elastic carry strap looped around a joint or similar convenient mooring point (when such a joint or mooring point is available) on the other side of the injury.

For example, the device (with examples of embodiments and applications as shown in FIGS. 1 to 10 herein disclosed) is relatively simple to use and is designed to substantially carry the load and/or substantially reduce the tension of an injured muscle, tendon or other soft tissue during activity or rest. Referring to FIG. 4, a primary anchor (1) is fitted to a healthy portion of soft tissue adjacent to the injured soft tissue. An elastic carry strap (2) is stretched around an adjacent joint or secondary anchor site (1a) on the other side of the injury. Both ends of the elastic carry strap (3, 4) are attached to the primary anchor so as to protect the injured tissue through the application of an external tension force provided by the carry strap (FIGS. 4 to 7). When a convenient secondary anchor site for a carry strap is unavailable, a second conventional anchor may be used and the carry strap may be replaced with a tie (FIG. 10).

The present invention has been found to result in a number of advantages, such as:

The present invention is a relatively simple and effective device for the protection and treatment of injured muscles, tendons and other soft tissue;

The present invention can be worn for relatively long periods of time, and/or during recuperative periods;

The present invention allows relatively good joint movement, which is normally restricted with rigid taping systems;

The present invention provides relatively good support to damaged tissue in different joint positions, whereas normally support is restricted to only one joint position with rigid taping systems;

The present invention provides an easily adjustable and controllable support force, whereas normally support force is difficult to adjust or control with rigid taping systems;

The present invention provides a support force which may be adjusted to encourage an optimum rate of healing of the injured soft tissue;

The present invention provides a relatively clean and non sticky support system;

The present invention is relatively comfortable compared to other support systems;

The present invention is relatively easy to fit and remove without assistance;

The present invention causes a relatively low restriction to muscle contraction compared to conventional support straps;

The present invention is relatively inexpensive.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, objects, advantages and aspects of the present application may be better understood by those skilled in the relevant art by reference to the following description of preferred embodiments taken in conjunction with the accompanying drawings, which are given by way of illustration only, and thus are not limitative of the present invention, and in which.

DETAILED DESCRIPTION

Normally when carrying a load the tension force in a muscle is transferred via the entire length of the muscle to its point of origin e.g. the lateral epicondyle for the forearm extensor muscle group. The present invention is designed to transfer this tension force from one side of any injured soft tissue (including tendon attachment sites) to the other, using elastic strap material to by pass the injured tissue and carry its load. This is achieved by blocking off (relatively isolating) the injured tissue with an anchor strap or similar device, which is attached to the elastic strap. The other end of the elastic strap is attached to the body with the simplest arrangement possible, preferably a carry strap (shaped like a stirrup) around a joint. Because the carry strap is made from elastic material, the anchor can move, however its movement is controlled by the tension in the carry strap, providing an ideal balance of protection of the injured tissue and normal function and movement of the body. It should be noted that damaged tissue requires a certain amount of movement for optimum healing when an injury is in, or has subsided to, the sub acute stage.

The present invention is considered to be better than a conventional tensioned strap (which is designed to restrict muscle contraction) because it provides an adjustable external force to carry the load of the injured tissue and protect it from excessive strain. The method is better than support taping because it provides good support through a wide range of joint positions, and it allows movement. The method is better than other designs using multiple straps and multiple anchors and mooring devices due to its simplicity, with the present invention using only one anchor and one elastic carry strap in its preferred embodiment for certain injuries.

The device in accordance with this invention has many variations and applications, some of which are illustrated in the accompanying drawings, wherein like numerals indicate the same elements throughout the views.

Figure 1:
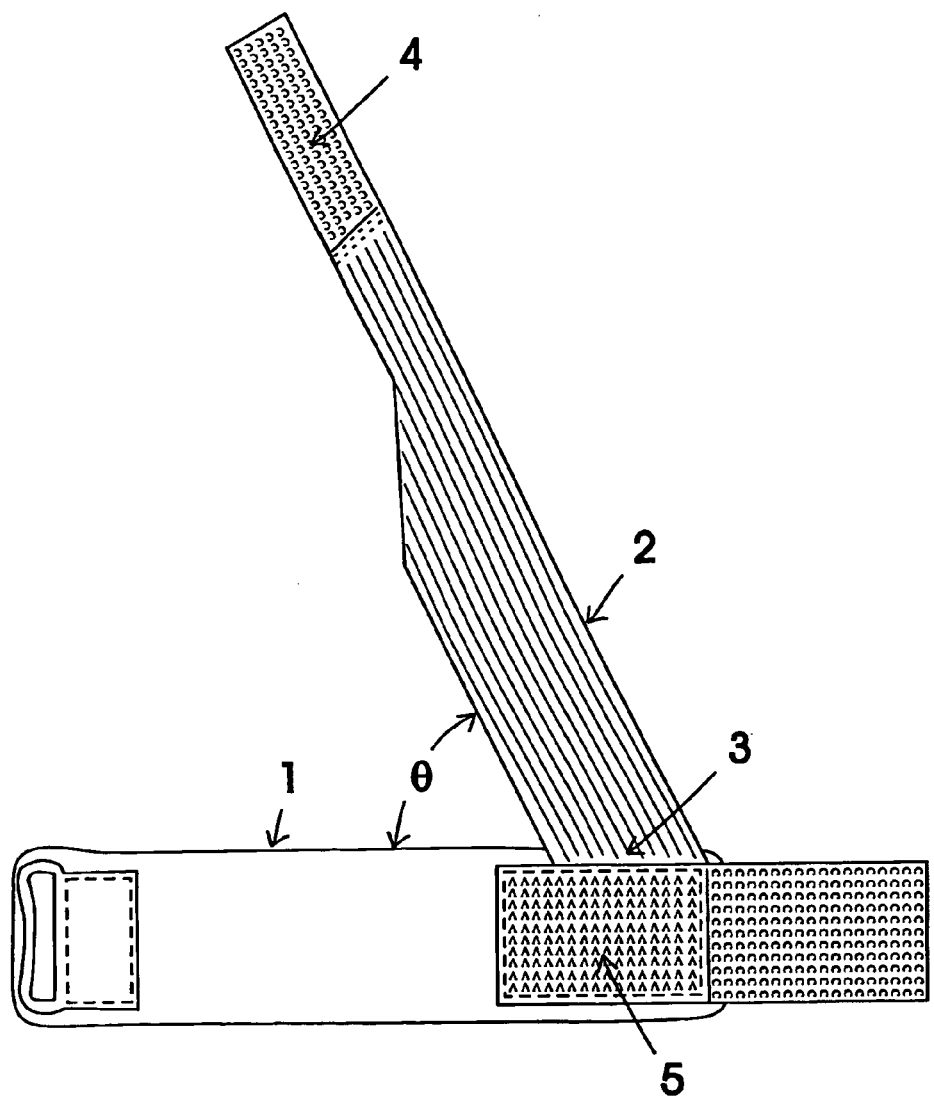
FIGS. 1, 2 and 3 illustrate three preferred embodiments of the device.
Figure 2:
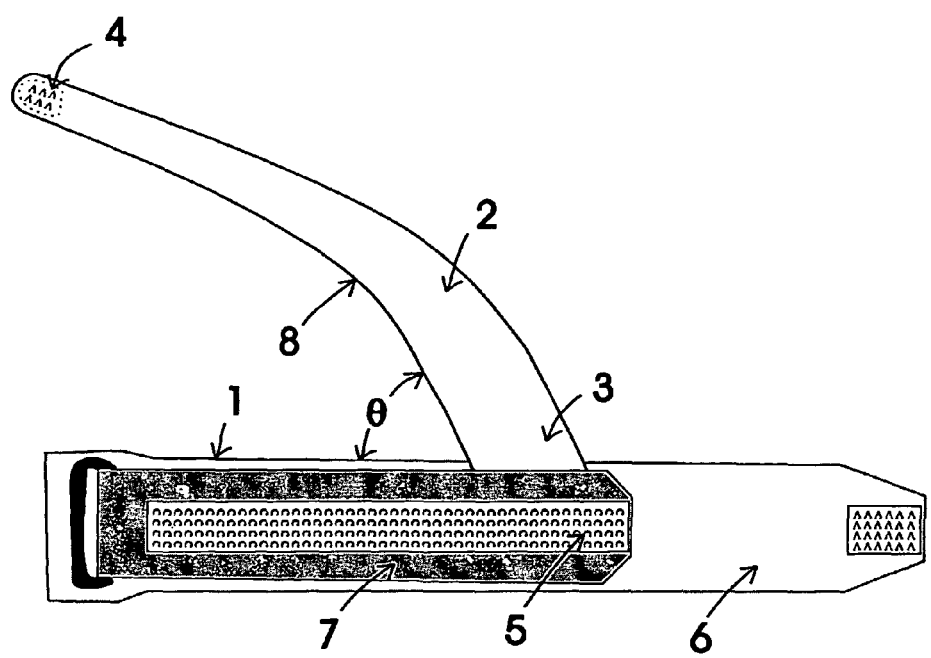
Figure 3:
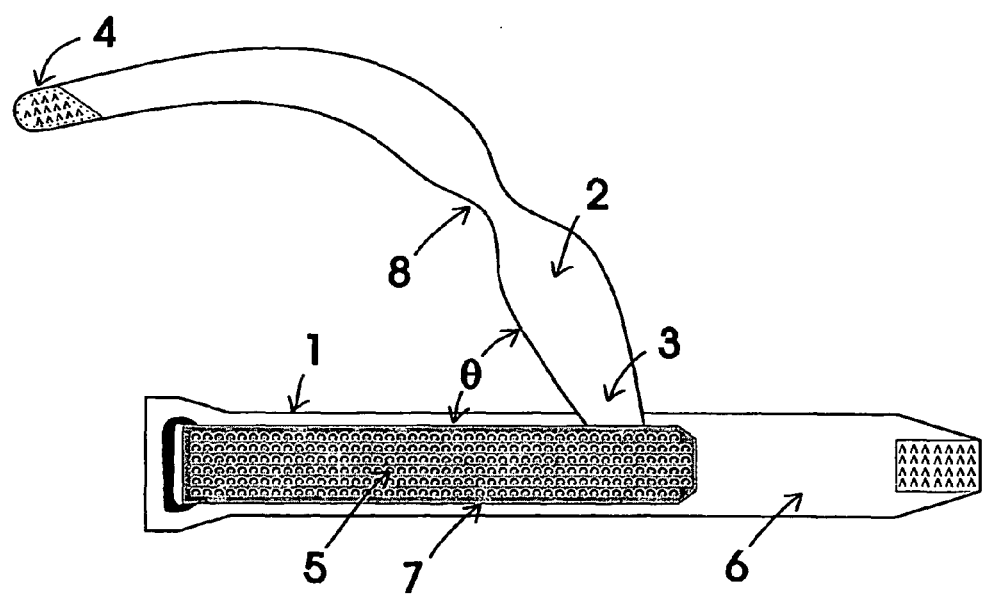
Figure 10:
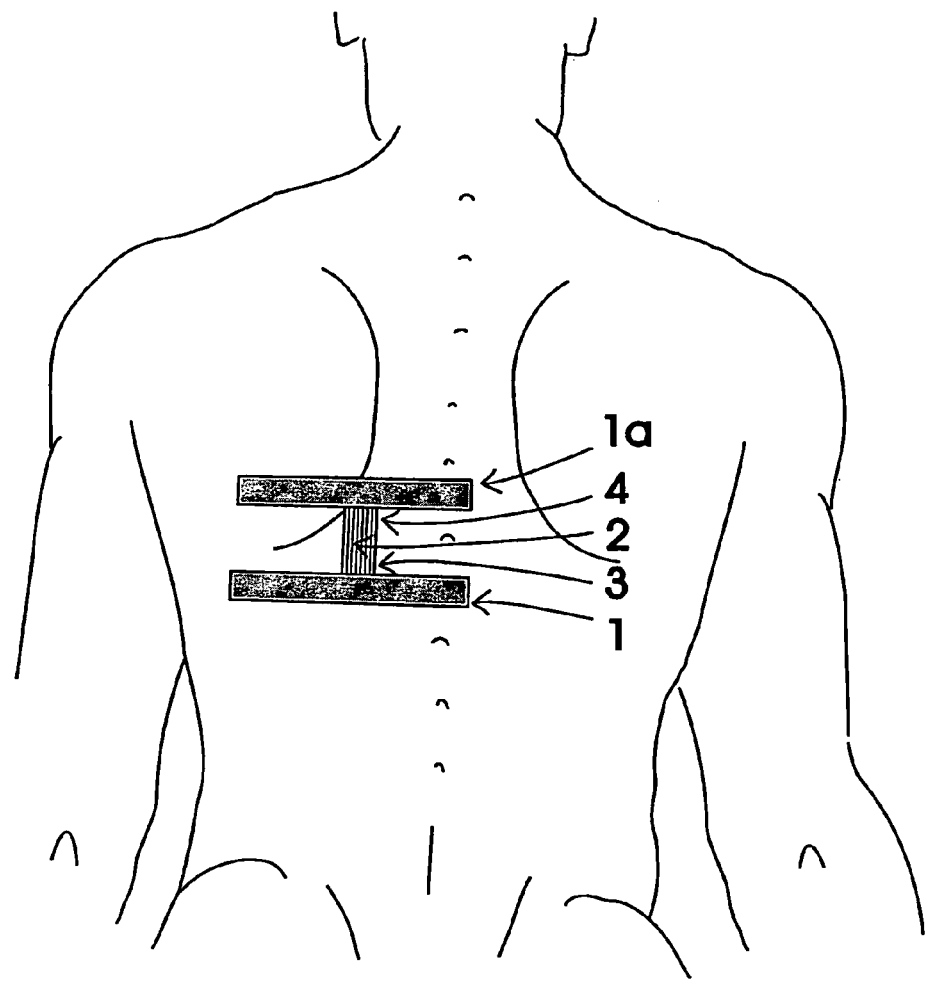
FIG. 10 is an illustration of another embodiment of the device, where the device has been properly placed on the back to treat a left erector spinae muscle injury.

A preferred embodiment of the present invention is shown in FIGS. 1, 2 and 3, in which a primary anchor (1) is fitted (locked) onto a healthy portion of soft tissue adjacent to injured soft tissue. An elastic carry strap (2) is stretched like a stirrup around an adjacent joint or secondary anchor site (1*a*) on the other side of the injury as shown in FIGS. 4 to 9. Both ends of the elastic carry strap (3, 4) are attached to a Velcro surface (5) of the primary anchor so as to protect the injured tissue through the application of an external tension force provided by the carry strap. When the body of the anchor strap (6) is made from soft material such as neoprene to provide more comfort, as shown in the embodiments in FIGS. 2 and 3, a substantial portion of the anchor strap is stiffened on the outside with a reinforcing strip of material (7) such as viny or Velcro so the anchor strap resists distortion and remains almost rigid on the body when moved by a tension force in the elastic carry strap. When a convenient secondary anchor site suitable for a carry strap is unavailable, a second conventional anchor is used and the carry strap can be used as a tie as shown in FIG. 10.

Conventional tension straps of the type currently in common use to restrict muscle contraction, including variations which provide heat or additional pressure to injured tissue, may be used as anchor components in the manufacture of the present device provided that they produce the desired outcome.

The anchors will preferably be made from soft, flexible non elastic material, but a number of other materials such as elastic materials and adhesive or non adhesive tape may be used, provided that they produce the desired outcome.

The elastic carry strap or tie is preferably made from a soft, stretchable elastic or fabric, but other materials that perform a similar function may be used.

The anchors and elastic carry strap or tie are fitted to ensure that they are comfortable and do not slip.

The elastic carry strap or tie is tensioned to provide the desired load carrying relief to the injured tissue.

The device, with a typical configuration as shown in FIGS. 1, 2 and 3, is used to protect injured muscles, tendons, ligaments, nerves, blood vessels and other soft tissue near to or remote from joints such as the wrist, elbow, shoulder, ankle, knee, hip, spine or other joints as depicted in, but not limited to, examples shown in FIGS. 4 to 10.

Figure 4:
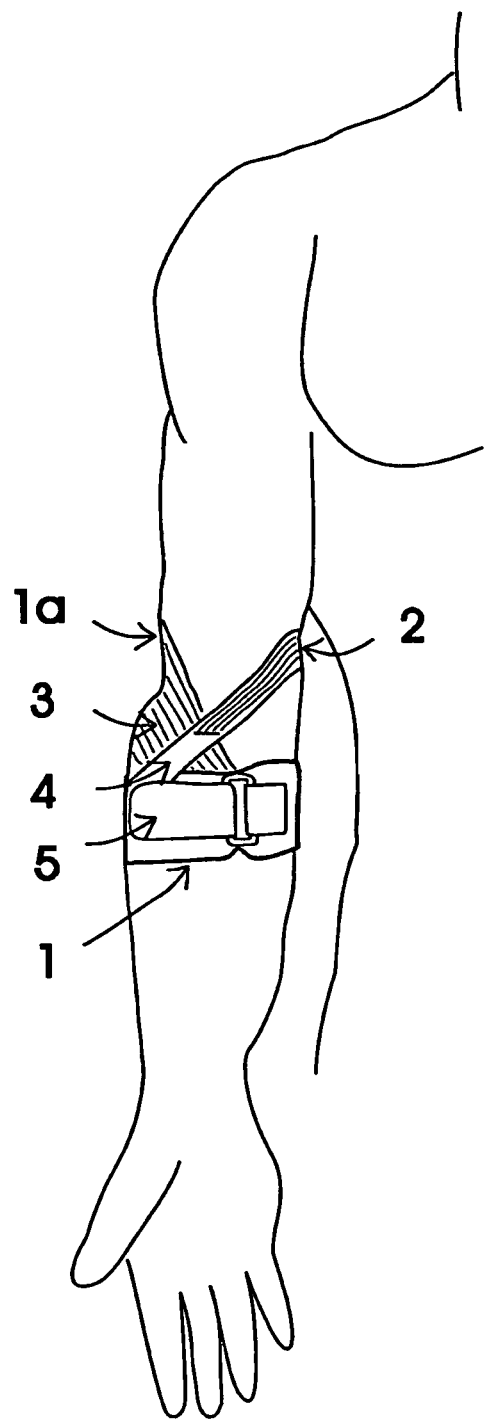
FIG. 4 illustrates the embodiment of the device shown in FIGS. 1, 2 and 3, but where the device has been properly placed on an injured right arm to treat tendonitis or lateral epicondylitis, for example.
Figure 5:
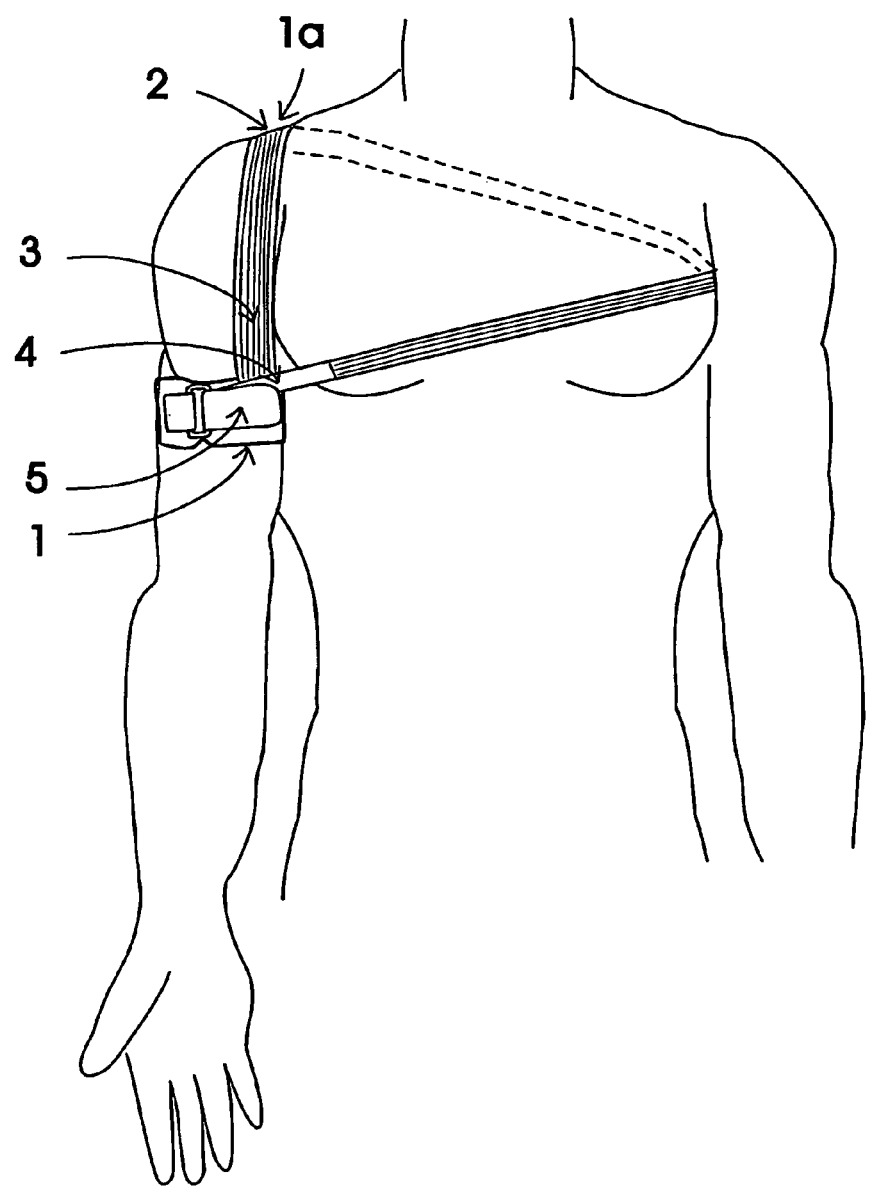
FIG. 5 is an illustration of another embodiment of the device, where the device has been properly placed on a right arm and body to treat a bicep tendon injury.
Figure 6:
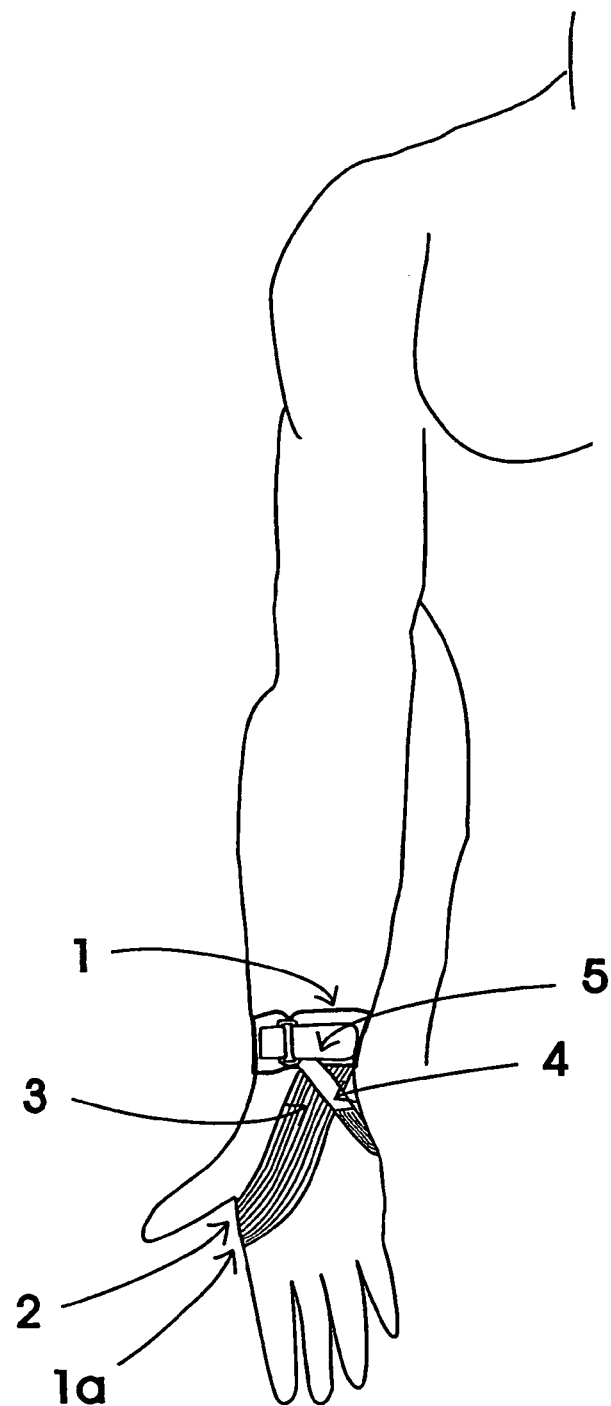
FIG. 6 is an illustration of another embodiment of the device, where the device has been properly placed on a right arm and hand to treat a carpal tunnel injury.

A preferred application for the device as shown in FIGS. 1, 2 and 3 is illustrated in FIG. 4.

The device is comfortable, provides good support in different joint or body positions, and in most instances as exemplified in FIGS. 4 to 9 can be quickly and easily applied or removed by the user.

The device can be worn to protect an injury during activities that would normally risk aggravation, and can also be continually worn during recuperative periods to provide a level of load carrying support which encourages an optimum rate of healing of the injured soft tissue.

The device requires only one conventional anchor to provide protection for certain injuries, typical examples shown in FIGS. 4 to 9. The anchor (1) is preferably made of flexible but non-elastic material.

The device uses an elastic carry strap (2) to provide a protective tension force between an anchor (1), which is fitted onto or around healthy tissue, and an anchor point (1*a*), which already exists on the body for certain cases as exemplified in FIGS. 4 to 9. For other cases, conventional anchors are required on both sides of an injury as exemplified in FIG. 10, and the elastic carry strap is replaced with an elastic tie. The tension in both the anchor strap and elastic tie or carry strap can be easily adjusted by the user to permit sporting activity, general activity or rehabilitation situations to occur.

Less tension is required in the anchor strap than normally required by a conventional tensioned strap, as the main support to the injury is provided by the elastic tie or carry strap. Consequently the device can be comfortably worn for long periods, e.g. all day at work, or longer.

Figure 7:
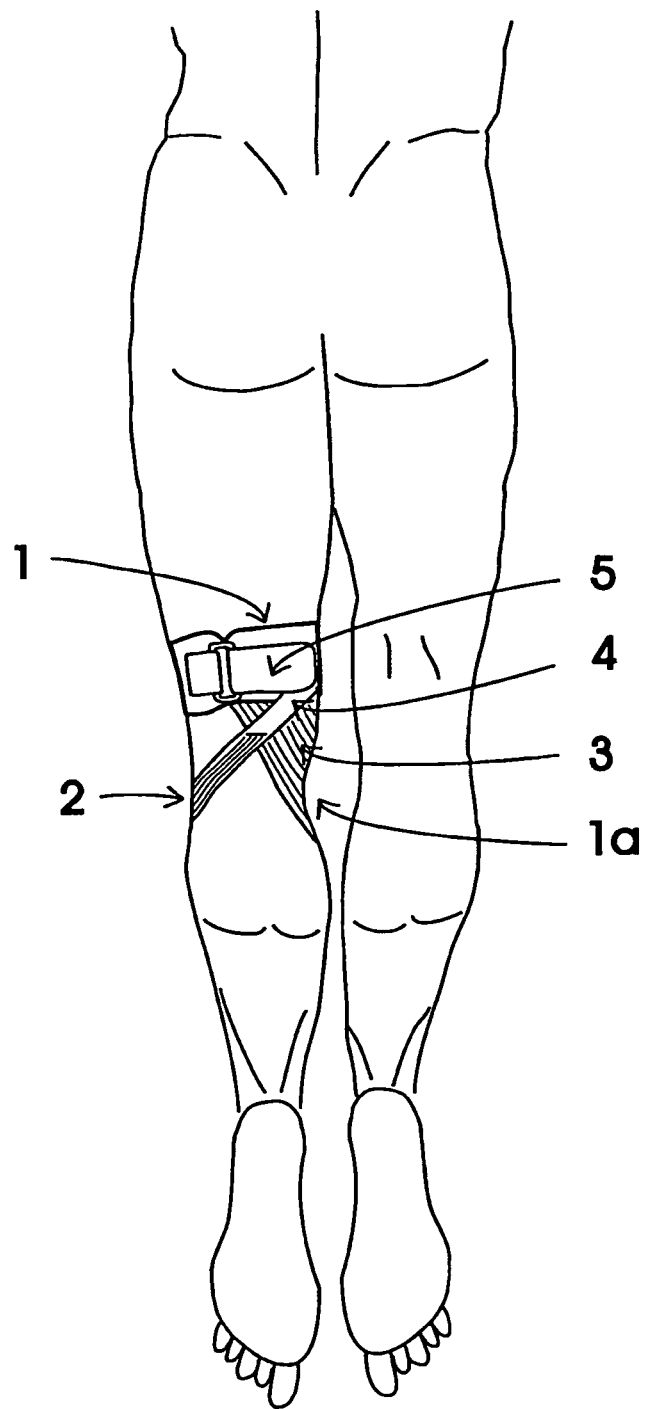
FIG. 7 is an illustration of another embodiment of the device, where the device has been properly placed on a left leg to treat a hamstring tendon injury.

For certain injuries as typically exemplified in FIGS. 4 and 7 the wider end of the elastic carry strap (3) can be aligned over the injury and additional support is provided via direct pressure on the injured tissue, holding this tissue in position and thus further helping to prevent it from stretching. An additional benefit is that injured tissue is also kept warm.

The device may be readily constructed using stitching and other standard processes of the clothing manufacturing industry.

The anchor strap and elastic tie or carry strap can be manufactured in a range of standard sizes and shapes for applications as depicted in, but not limited to, examples shown in FIGS. 4 to 10, and provided with adjustability within these sizes by a suitable fastening device, typically Velcro.

The anchor strap is preferably made from soft, flexible and substantially inelastic material with the characteristic that it resists distortion and remains almost rigid on the body when moved toward the secondary anchor site by a tension force in the elastic carry strap or tie of 10 Newton. It should be noted that in the present invention the objective of the anchor is to lock onto healthy tissue beside injured tissue. This can also be achieved with non rigid (elastic) anchor material, however more rigid material in the region of the injury would increase the extent of the protection.

The anchor strap preferably includes a flexible, elongated band-like body and a selectively adjustable fastener system to hold the opposed ends of the body in a secured overlapping relationship to provide a closed adjustable loop encompassing the part of the anatomy around which it is fitted, however other anchor designs and other suitable materials can also be used to achieve the desired outcome.

The width of the anchor strap will preferably range anywhere from 5 to 100 millimetres depending on the application. Smaller diameters generally require less strap width to achieve a stable anchor which resists distortion. For the embodiment of the device shown in FIGS. 1 to 4 the width of the anchor will preferably be between 40 to 70 millimetres, but variations outside this range may be possible with different materials.

The elastic tie or carry strap will preferably be made from soft elastic material, however other suitable materials can also be used to achieve the desired outcome.

The elastic tie or carry strap material will preferably have relatively large elastic qualities in a longitudinal direction along a length of the said material, and relatively small elastic qualities in a transverse direction across a width of the said material.

The coefficient of stiffness of the elastic tie or carry strap material will preferably be similar to that typically used in underwear support elastic. A 50 millimetre wide strap of the elastic material used will preferably develop a tension force of between 5 to 15 Newton when elongated to 150% of its resting length, but materials with characteristics outside this range may also be used to achieve the desired outcome.

As can be seen in the examples shown in FIGS. 4 to 10, the angle of attachment Θ of the elastic carry strap (2) to the anchor (1) will vary with the location of the injury. This angle could range anywhere from 30 to 150 degrees, and is designed so that the carry strap provides a relatively even pull across its full width, thereby optimizing comfort and support. Typically the widest end (3) of the elastic carry strap would be sewn or otherwise permanently fastened onto an anchor strap (1) at a particular angle such as that shown in FIGS. 1, 2 and 3 to cater for a particular injury, e.g. lateral epicondylitis or tennis elbow as shown in FIG. 4, where the angle of attachment is preferably around 55 to 60 degrees. An alternative embodiment of the device with detachable Velcro or other fastening system at both ends of the carry strap or tie would be useful to allow different attachment angles for different injuries, and so that the attachment angle and position can also be adjusted by the user to optimize comfort and support. A fastening system on both sides of the components would allow for reversing the attachment angle for left and right injuries.

The elastic carry strap or tie can be made as a separate item to be used in conjunction with separate anchor straps or adhesive tape anchors.

The elastic tie can be manufactured already joined to one or two anchor straps or adhesive tape anchors.

In the present invention, it has been found important that the width of the elastic carry strap (2), including its ends (3, 4) be in a particular range of dimensions for optimum comfort, fit and support. For the embodiment of the device shown in FIGS. 1 to 4 the wide end of the carry strap (3) will preferably be in a range between 40 and 60 millimetres at the widest portion, with the preferred dimension being 50 millimetres. It has been found that when this portion of the carry strap has a lesser width, it does not give the desired distribution of support pressure over the injured tissue, and that a greater width results in a loose fit so as to restrict the benefits of the present invention. The narrow end of the carry strap (4) in this embodiment will preferably be in the range 15 to 30 millimetres, with the preferred dimension being 22 millimetres, this smaller dimension being better to minimize irritation in the crease of the elbow.

A curved shape (8) to provide a more comfortable fit can be used to achieve the embodiments of the device shown in FIGS. 2 and 3 by cutting the elastic carry strap from a 75 or 100 millimetre wide elastic strip. Narrowed sections (3, 8) in the curved shape as shown in FIG. 3 can be used to provide a more comfortable fit through a bigger range of joint positions due to the ability of the narrowed sections to change shape more easily.

For the embodiment of the device shown in FIGS. 1 to 4 the length of the widest portion of the carry strap (3) will preferably be between 100 and 130 millimetres or greater, and be sufficiently long to fully cover the injured tissue.

The edges of tapered portions of elastic material will preferably be overlocked or otherwise protected from fraying.

The variation in width of the elastic carry strap (2) over its length will be different for different embodiments of the device as depicted in examples shown in FIGS. 4 to 10, and could range anywhere from 5 to 100 millimetres. The widest end of the carry strap is preferably to be placed over the injured tissue so as to maximize contact between the elastic carry strap and the injured soft tissue.

The length of the elastic tie or carry strap will vary considerably depending on its location on the body. For the embodiment of the device shown in FIGS. 1 to 4 the length of the elastic carry strap (2), excluding the length of its fastening surfaces, will preferably be in a range between 200 and 350 millimetres, with the preferred dimension being derived from the formula of 75 millimetres plus 75% of the circumference of the widest part of the forearm. It has been found that when a carry strap with the preferred elasticity (coefficient of stiffness) has a length greater than that derived from the above formula, it does not give the desired support tension, and that a carry strap with a lesser length results in too much tension and not enough freedom of joint movement so as not to achieve the objectives of the present invention. The length of the elastic carry strap is preferably within 10% of that calculated from the above formula.

A variation in attachment positions (5) for the carry strap or tie will preferably be provided to allow a method for altering the effective length of the carry strap or tie, and also to ensure that in all cases the carry strap will stay in place and also provide good support. Depending on the location of the injury, these attachment positions may vary widely, e.g. for the embodiment of the device shown in FIG. 8. Support for rotator cuff injuries, refer FIG. 5, can be provided by using an attachment position further around the arm either anteriorly, or posteriorly via the axilla to protect against external or internal rotation respectively.

The method of fitting can be varied to suit the various fastening systems available for attaching the ends of the elastic carry strap (3, 4). For rigid or elastic adhesive tape anchors as shown in FIG. 10, a second layer of tape would provide a simple and effective method of locking down the ends of the elastic tie or carry strap. For a prefabricated anchor strap and carry strap with Velcro fastening system as shown in FIGS. 1 to 4, a typical method of fitting would be:

Align the widest end (3) of the elastic carry strap over the tendon or injury to be protected.
  Fasten the anchor strap over a healthy part of soft tissue with a light tension.
  Stretch the elastic carry strap around the adjacent joint or secondary anchor point to provide the desired unloading force.
  Attach the Velcro portion of the free end of the elastic carry strap (4) onto an unused portion of the Velcro fastening surface of the anchor strap (5).
  Check the tension in both the strap and the carry strap, and adjust if necessary.

Figure 8:
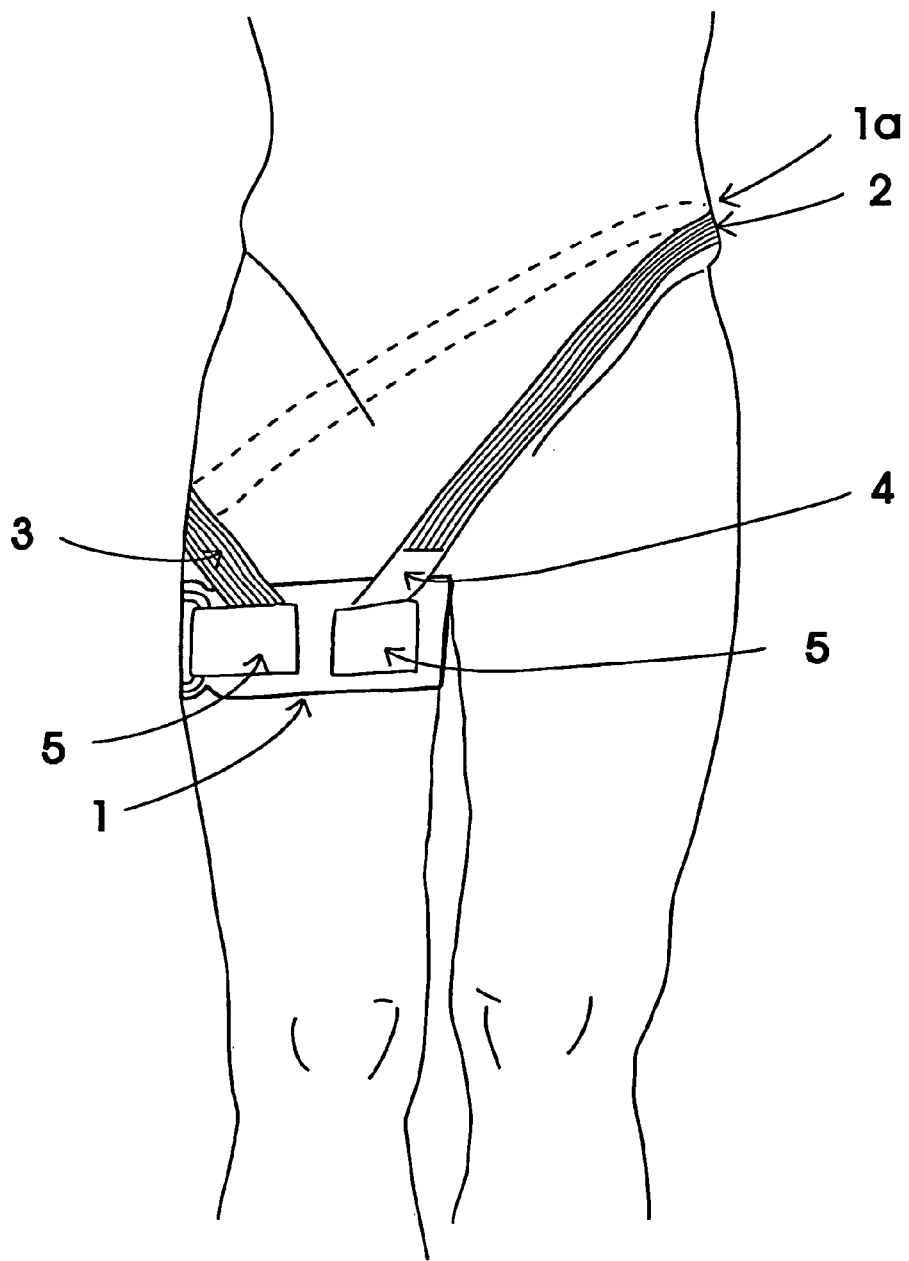
FIG. 8 is an illustration of another embodiment of the device, where the device has been properly placed on a right leg and body to treat a hip flexor injury.
Figure 9:
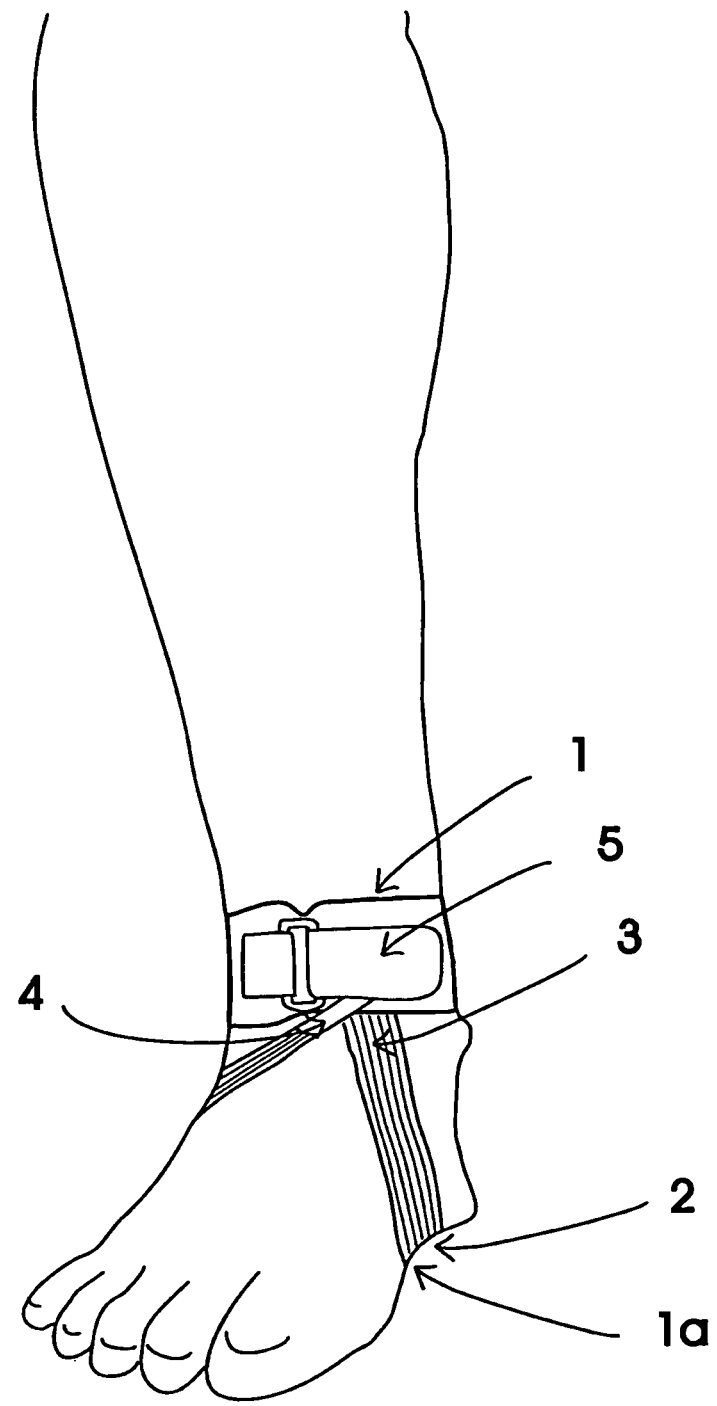
FIG. 9 is an illustration of another embodiment of the device, where the device has been properly placed on a right leg and foot to treat a tibealis anterior tendon injury.

Clearly the order of these steps can be varied, and may be different when the end of the elastic carry strap (4) is attached to a different portion of the anchor strap, e.g. as in FIG. 8.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The claims defining the invention are as follows:

1. A device for carrying a load and/or reducing tension of injured soft tissue associated with an arm while allowing movement of the injured soft tissue associated with said arm and providing support through a wide range of elbow positions, the device comprising:
   an anchor comprising a strap for securing around only a first body portion, the first body portion including only healthy tissue disposed adjacent to both the injured soft tissue and an associated elbow, and
   a carry strap extending to a second body portion and having an elastic portion, the carry strap having a first end and a second end connected to the said anchor at an angle substantially between 30 and 150 degrees
   wherein the injured soft tissue and the associated elbow both are disposed between the first body portion and the second body portion, and
   wherein the amount of load carried and/or the tension applied to the injured soft tissue can be changed by adjusting the position of attachment of the second end of the carry strap.

2. A device as claimed in claim 1, wherein the elastic portion is soft elastic material.

3. A device as claimed in claim 1, wherein the anchor is substantially soft, flexible and non elastic.

4. A device as claimed in claim 1, wherein the carry strap has a width of substantially between 5 and 100 millimeters.

5. A device as claimed in claim 1, wherein the elastic portion has a curved shape.

6. A device as claimed in claim 1, wherein the elastic portion is a stretchable fabric.

7. A method of enabling support of a portion of a human body, utilizing the device as claimed in claim 1, said method including steps of:
   securing said anchor around said first body portion;
   attaching said first end of said carry strap to said anchor;
   extending said carry strap around said second body portion wherein said portion of said body to be supported is disposed between said first body portion and said second body portion; and
   attaching said second end of said carry strap to said anchor.

8. A device as claimed in claim 1, wherein the elastic portion has one or more narrowed sections.

9. A device as claimed in claim 1, wherein the carry strap is releasably connected to the anchor.

* * * * *